United States Patent [19]

Barlet et al.

[11] Patent Number: 4,678,503
[45] Date of Patent: Jul. 7, 1987

[54] CONCENTRATED AQUEOUS SUSPENSIONS BASED ON NEBURON

[75] Inventors: Denis Barlet, Lyons; Dini Alain, Villefranches, both of France

[73] Assignee: Rhone-Poulenc Agrochimie, Lyons, France

[21] Appl. No.: 407,464

[22] Filed: Aug. 12, 1982

[51] Int. Cl.⁴ .............................................. H01D 25/22
[52] U.S. Cl. ........................................ 71/93; 71/108; 71/120; 71/124; 71/DIG. 1
[58] Field of Search .............. 71/120, 93, 108, DIG. 1

[56] References Cited

U.S. PATENT DOCUMENTS 3,399,991  9/1968  Littler .................................... 71/120

OTHER PUBLICATIONS

Kirk-Othmer, *Encyclopedia of Chemical Technology*, Third Ed., vol. 12, "Gravity Concentration to Hydrogen Energy", John Wiley and Sons, New York, pp. 299-302.

Eder. Fr. Demande 2,174, Oisg. Chem. Abst. vol. 81, (1974) 34581.

Primary Examiner—Catherine L. Mills
Attorney, Agent, or Firm—Browdy and Neimark

[57] ABSTRACT

Herbicidal compositions based on neburon.

These are concentrated aqueous suspensions containing, in addition to neburon and the usual wetting, dispersing and thickening adjuvants, a stabilizer of the formula:

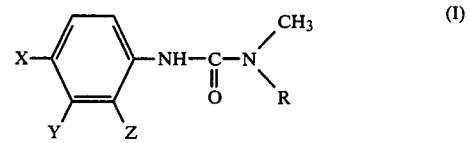

in which:
X, Y and Z are identical or different and are H, halogen or $C_1$-$C_4$-alkyl and R is $C_1$-$C_3$-alkyl.

The compositions can be used for selectively killing weeds in crops.

14 Claims, No Drawings

CONCENTRATED AQUEOUS SUSPENSIONS BASED ON NEBURON

The present invention relates to new herbicidal compositions, to their preparation and to their application. In particular, the present invention relates to new concentrated aqueous suspensions based on neburon.

Neburon, the common name for 1-(3,4-dichlorophenyl)-3-methyl-3-n-butylurea, is a known herbicide, in particular for selectively killing weeds in crops, especially cereals and in particular by the pre-emergence method.

Commercial herbicidal compositions based on neburon have for a long time been in the form of wettable powders. However, for some years attempts have been made to develop liquid compositions based on this active ingredient, in particular concentrated aqueous suspensions, which have important advantages, such as easy storage (reduced volume), easy handling (absence of dust) and ease of application (easier dispensing).

Certain compositions of this type have been proposed, which, in addition to neburon, by itself or as a mixture with in general at least one other herbicide, contain a thickener and at least one wetting and/or dispersing surface-active agent.

However, these compositions are physically unstable and, after having been stored for only a few months, thicken with sedimentation and irreversible formation of a paste which can, if the storage temperature rises, turn into a completely solid mass. Thus, when the composition has been dispersed in water at the time of use, it cannot be re-suspended, or can be re-suspended only with difficulty; at best, the solid particles in the dilution can have a diameter sufficiently large to cause blockage of the pulverisation nozzles.

Liquid herbicidal compositions based on neburon which are highly stable on storage, even for prolonged periods, have now been found.

The invention thus relates to new concentrated aqueous suspensions based on neburon containing, as adjuvants, in the conventional manner, a thickener, at least one wetting agent and/or at least one dispersing agent, which suspensions also contain from 1 to 10%, preferably from 2 to 6%, by weight, based on the neburon, of a stabiliser of the formula:

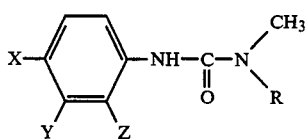

in which:

X, Y and Z are identical or different and each represents a hydrogen atom, a halogen atom or an optionally halogenated alkyl radical containing from 1 to 4 carbon atoms and R represents an alkyl radical containing from 1 to 3 carbon atoms.

Preferred compositions contain, as the specific stabiliser, a compound of the formula:

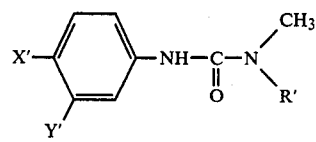

in which:

R' represents a methyl or ethyl radical, X' is a hydrogen or halogen atom (preferably chlorine or bromine) or an alkyl radical containing from 1 to 4 carbon atoms and Y' is a hydrogen or halogen atom (preferably chlorine or bromine) or a trifluoromethyl radical, at least one of these two substituents X' and Y' preferably being a halogen atom.

Good results have been obtained with stabilisers of the general formula (II) in which X' is a chlorine or bromine atom or a methyl radical and Y' is either hydrogen, if X' is a chlorine or bromine atom, or a chlorine or bromine atom.

The content of stabiliser according to the invention is usually between 1 and 10% by weight, based on the neburon. Amounts of less than 1% are generally incapable of providing the concentrated aqueous suspensions with sufficient stability. Moreover, amounts greater than 10% do not improve the stabilising effect and are unfavourable from an economic point of view. In addition, they may have the disadvantage of achieving doses which cause an adverse secondary herbicidal effect.

In these compositions, at least 95% by weight of the solid particles in suspension have a diameter of less than 20 microns, 50% by weight having a diameter equal to at most 7 microns and preferably equal to at most 5 microns.

The herbicidal compositions according to the invention contain, as the active ingredient, neburon, by itself or as a mixture with other complementary herbicides, such as, e.g., diphenyl ether derivatives, such as nitrofen and bifenox, ureas, such as isoproturon, triazines, such as terbutryn and atrazine, dinitroamines, such as pendimethalin, or any other herbicide which does not appreciably modify the stability of the neburon according to the invention.

The concentrations of neburon in the formulations according to the invention vary within the range from 100 g/l to 600 g/l, preferably from 200 g/l to 500 g/l, which is that generally used. Taking into account the proportions defined above, these suspensions thus contain from 0.2 to 3.6%, preferably from 0.25 to 3%, by weight of stabiliser.

The thickeners used in the compositions according to the invention are products which, when added to water or to aqueous solutions or suspensions of pesticides, impart pseudoplastic properties to the latter.

The thickeners which can be used in the invention may be mineral or organic in nature.

Thickeners of the mineral type which may be mentioned are attapulgites, bentonites, laponites and colloidal silicas.

Thickeners of the organic type which may be mentioned are alginates, and especially hydrophilic biopolymers of the heteropolysaccharide type, these biopolymers being the preferred thickeners according to the invention.

The amount of thickener in the compositions according to the invention is generally between 0.01 and 15% by weight, and advantageously between 0.05 and 10% by weight. In the case where the thickener is a hydrophilic, heteropolysaccharide biopolymer, the amount of thickener is generally between 0.01 and 2% by weight, preferably between 0.05 and 0.5% by weight.

The hydrophilic biopolymers of the heteropolysaccharide type which can be used in the invention are known products. They have a molecular weight greater than 200,000, and preferably greater than 1,000,000; they have pseudoplastic properties and are usually obtained by the action (i.e. by fermentation) of bacteria of the Xanthomonas family on carbohydrates. These biopolymers are also sometimes known by other quite diverse expressions, such as: hydrophilic colloids of Xanthomonas; heteropolysaccharide gums; xanthan gums; or extracellular heteropolysaccharides originating from Xanthomonas or from bacteria of the Pseudomonas family. The word biopolymer is used in the sense that it means polymers produced by a biological process (in this case bacterial fermentation).

The bacteria used for preparing these biopolymers are usually *Xanthomonas campestris*, but it is also possible to use other Xanthomonas species, such as *Xanthomonas carotae*, *Xanthomonas incanae*, *Xanthomonas begoniae*, *Xanthomonas malvacearum*, *Xanthomonas vesicatoria*, *Xanthomonas translucens* and *Xanthomonas vasculorum*. Suitable carbohydrates for fermentation with the aid of Xanthomonas bacteria are glucose, sucrose, fructose, maltose, lactose, galactose, starch, potato starch and the like.

In addition to the above type of thickener, the compositions according to the invention contain the surface-active agents usually employed in the preparation of concentrated aqueous suspensions, i.e. at least one wetting agent and at least one dispersing agent. These two properties may be found in the same product, in which case, by way of simplification, a single agent having a mixed action can be employed.

Suitable wetting agents are preferably those of the non-ionic type, such as an ethylene oxide/(poly)alkylphenol condensate, an ethylene oxide/polyarylphenol condensate, an ethylene oxide/alcohol condensate or an ethylene oxide/fatty amine condensate. This compound is generally present in the concentrated aqueous suspensions in an amount from 0.5 to 5%, preferably from 1 to 3%, by weight.

Suitable dispersing surface-active agents are generally those of the anionic type, such as, e.g., salts of strong acids, such as phosphates or sulphonates, and condensates (usually 8–20:1 condensates) of ethylene oxide with alkylphenols, polyalkylphenols or polyarylphenols. This dispersing agent is generally present in the concentrated aqueous suspensions in an amount from 0.5 to 5%, preferably from 1 to 3%, by weight.

The concentrated aqueous suspensions according to the invention can also advantageously contain other conventional adjuvants, such as an anti-freeze (in an amount from 5 to 10% by weight), an anti-foaming agent, such as emulsions of a silicone oil or of a fatty alcohol (in an amount from 0.2 to 1% by weight), or also, if the thickener is a biopolymer, a preservative (in an amount from 0.1 to 0.5% by weight), such as a composition based on formaldehyde.

The compositions according to the invention can be prepared in, e.g., two stages.

The first stage consists in adding the wetting agent, the dispersing agent and, if necessary, the anti-freeze to water.

In the second stage, neburon and, if appropriate, the complementary herbicide or herbicides, as well as the stabiliser, are dispersed, with stirring, in the aqueous composition obtained. The suspension obtained is then comminuted in a mill, for example a ball mill, such as the mill sold under the trademark DYNOMILL. If the thickener is mineral in nature, it is added as such in the second stage.

On the other hand, if the thickener is a biopolymer, it is added in the form of a predispersion in a small amount of water containing the preservative (for example formaldehyde in 40% strength aqueous solution).

The examples which follow are given without implying a limitation to illustrate the preparation and the composition of the concentrated aqueous suspensions according to the invention, as well as their improved stability on storage in comparison with known formulations.

EXAMPLE 1

An ethylene oxide/alkylphenol condensate (13:1), as the wetting agent, a salt of a phosphated ethylene oxide/alkylphenol condensate (9:1), as the dispersing agent, and glycol, as the anti-freeze, are first introduced into water. Neburon and 3-(3,4-dichlorophenyl)-1,1-dimethylurea are then added, with stirring, to the composition obtained. The suspension obtained is comminuted in a ball mill (trademark DYNOMILL). A predispersion of the hydrophilic, heteropolysaccharide biopolymer and of a silicone oil having an anti-foaming action, in an aqueous solution containing formaldehyde (preservative), is then added, with stirring. The amounts used are calculated such that the following composition, by weight, is obtained:

| | |
|---|---|
| neburon | 36.4% |
| glycol (anti-freeze) | 5% |
| wetting agent | 2.5% |
| dispersing agent | 2.5% |
| anti-foaming agent | 0.4% |
| preservative | 0.3% |
| thickener | 0.2% |
| stabiliser | 1% |
| water | q.s.p. 100% |

In this formulation, the stabiliser is 3-(3,4-dichlorophenyl)-1,1-dimethylurea; its content by weight, based on neburon, is 2.75%.

An analogous composition is also prepared by the same procedure, except that it does not contain a stabiliser according to the invention.

Each of these compositions is subjected to three tests, in each case at time to, after one month at 50° C. in an oven, and after a period of 5 weeks in an oven at a variable temperature with a weekly cycle of 4 days at +35° C. followed by 3 days at −10° C. (freeze/thaw, or F/T, test). The three tests used are as follows:

(1) Self-dispersion test: the concentrated suspension (5 g) is poured into a 250 ml test-tube filled with water. The course of the dispersion is rated according to the following scale:
  dispersion starting at the first drop: very good (v.g.)
  the product precipitates as dispersed flocks: mediocre (m)
  the product precipitates as compact lumps: zero (0).

(2) The dynamic viscosity, expressed in centipoises (measured with the aid of a RHEOMAT 30 rotary viscosimeter from CONTRAVES) is measured.

(3) The mean diameter of the particles is measured with the aid of a COULTER-COUNTER (cumulative percentage by weight).

Table (I) shows the results obtained for each suspension tested, each test being carried out at each of the three times chosen.

These results clearly show that:

(1) at time to, the two suspensions have the same properties, (2) after 30 days at 50° C., the known suspension is no longer self-dispersible or pourable, which corresponds to a very significant increase in the diameter of the particles, whilst the suspension containing the stabiliser according to the invention keeps its excellent starting properties, (3) the known suspension exhibits poor behaviour in the freeze/thaw test, whereas the suspension stabilised according to the invention retains its excellent initial properties.

EXAMPLE 2

Analogous results are obtained if the 3-(3,4-dichlorophenyl)-1,1-dimethylurea used as the stabiliser in the composition according to the invention described in Example 1 is replaced by an equal amount of 3-(4-chlorophenyl)-1,1-dimethylurea, 3-(3-chloro-4-methylphenyl)-1,1-dimethylurea, 3-(3-bromophenyl)-1,1-dimethylurea, 3-(4-bromophenyl)-1,1-dimethylurea, 3-(4-methylphenyl)-1,1-dimethylurea or 3-(3-chloro-4-methylphenyl)-1-methyl-1-ethylurea.

EXAMPLE 3

The following compositions, expressed by weight, are prepared using the same procedure as in Example 1:

|  | 3A | 3B |
| --- | --- | --- |
| neburon | 25% | 45% |
| anti-freeze | 5% | 6% |
| wetting agent | 2% | 3% |
| dispersing agent | 1.5% | 2.5% |
| anti-foaming agent | 0.3% | 0.5% |
| preservative | 0.3% | 0.3% |
| thickener | 0.2% | 0.2% |
| stabiliser | 0.5% | 1.5% |
| (i.e. 3.3% by weight, relative to neburon) | | |
| water | q.s.p. 100% | |

In these formulations, 3-(3,4-dichlorophenyl)-1,1-dimethylurea, 3-(4-chlorophenyl)-1,1-dimethylurea and 3-(3-chloro-4-methylphenyl)-1,1-dimethylurea were used in succession as the stabiliser; the amount by weight of 0.5%, relative to the formulation, corresponds to an amount of 2% by weight, relative to neburon; the amount by weight of 1.5%, relative to the formulation, corresponds to an amount of 3.3% by weight, relative to neburon.

EXAMPLE 4

The following composition, expressed by weight, is prepared using the same procedure as in Example 1:

| neburon | 23% |
| --- | --- |
| isoproturon | 23% |
| anti-freeze | 5% |
| wetting agent | 2.5% |
| dispersing agent | 1.5% |
| anti-foaming agent | 0.5% |
| thickener | 0.2% |
| preservative | 0.3% |
| stabiliser | 0.5% |
| water | q.s.p. 100% |

In this formulation, 3-(3,4-dichlorophenyl)-1,1-dimethylurea, 3-(4-chlorophenyl)-1,1-dimethylurea, 3-(3-chloro-4-methylphenyl)-1,1-dimethylurea, 3-(3-bromophenyl)-1,1-dimethylurea, 3-(4-bromophenyl)-1,1-dimethylurea, 3-(4-methylphenyl)-1,1-dimethylurea and 3-(3-chloro-4-methylphenyl)-1-methyl-1-ethylurea are used in succession as the stabiliser; the amount of stabiliser by weight, relative to neburon, is 2.2%.

The dispersing agent in this formulation is a salt of a phosphated ethylene oxide/polyarylphenol condensate (about 18:1).

This suspension is subjected to the same tests as those described in Example 1, in comparison with an analogous suspension containing no stabiliser according to the invention. The results are shown in Table (II).

The same remarks as for Example 1 may be made, and it may also be stated that the stabilising effect is not altered by the presence of isoproturon.

EXAMPLE 5

The procedure followed is as in Example 4, except that, all other things being equal, the amount of stabiliser is varied.

| % of stabiliser, relative to the formulation | 0.3 | 0.75 | 1 | 2 | 2.5 |
| --- | --- | --- | --- | --- | --- |
| % of stabiliser, relative to neburon | 1.2 | 3 | 4 | 8 | 10 |

EXAMPLE 6

The concentrated aqueous suspension having the following composition by weight is prepared using the same procedure as in Example 1:

| neburon | 20% |
| --- | --- |
| isoproturon | 15% |
| bifenox | 15% |
| anti-freeze (glycol) | 5% |
| wetting agent | 1.5% |
| dispersing agent | 1% |
| anti-foaming agent | 0.3% |
| thickener | 0.2% |
| preservative | 0.3% |
| stabiliser | 0.5% |
| water | q.s.p. 100% |

In this formulation, 3-(3,4-dichlorophenyl)-1,1-dimethylurea, 3-(4-chlorophenyl)-1,1-dimethylurea, 3-(3-chloro-4-methylphenyl)-1,1-dimethylurea, 3-(3-bromophenyl)-1,1-dimethylurea, 3-(4-bromophenyl)-1,1-dimethylurea, 3-(4-methylphenyl)-1,1-dimethylurea and 3-(3-chloro-4-methylphenyl)-1-methyl-1-ethylurea are used in succession as the stabiliser; the amount by weight of stabiliser, relative to neburon, is 2.5%.

EXAMPLE 7

The concentrated aqueous suspension having the following composition by weight is prepared using the same procedure as in Example 1:

| neburon | 25% |
| --- | --- |

-continued

|   |   |
|---|---|
| nitrofen | 20% |
| anti-freeze (glycol) | 5% |
| wetting agent | 3% |
| dispersing agent | 2% |
| anti-foaming agent | 0.3% |
| thickener | 0.2% |
| preservative | 0.3% |
| stabiliser | 0.5% |
| water | q.s.p. 100% |

In this formulation, 3-(3,4-dichlorophenyl)-1,1-dimethylurea, 3-(4-chlorophenyl)-1,1-dimethylurea, 3-(3-bromophenyl)-1,1-dimethylurea, 3-(4-bromophenyl)-1,1-dimethylurea, 3-(4-methylphenyl)-1,1-dimethylurea and 3-(3-chloro-4-methylphenyl)-1-methyl-1-ethylurea are used in succession as the stabiliser; the amount by weight of stabiliser, relative to neburon, is 2%.

EXAMPLE 8

The concentrated aqueous suspension having the following composition by weight is prepared using the same procedure as in Example 1:

|   |   |
|---|---|
| neburon | 25% |
| atrazine or terbutryn | 15% |
| anti-freeze | 5% |
| wetting agent | 2% |
| dispersing agent | 2% |
| anti-foaming agent | 0.4% |
| thickener | 0.2% |
| preservative | 0.3% |
| stabiliser | 1% |
| water | q.s.p. 100% |

In this formulation, 3-(3,4-dichlorophenyl)-1,1-dimethylurea, 3-(4-chlorophenyl)-1,1-dimethylurea, 3-(3-chloro-4-methylphenyl)-1,1-dimethylurea, 3-(3-bromophenyl)-1,1-dimethylurea, 3-(4-bromophenyl)-1,1-dimethylurea, 3-(4-methylphenyl)-1,1-dimethylurea and 3-(3-chloro-4-methylphenyl)-1-methyl-1-ethylurea are used in succession as the stabiliser; the amount by weight of stabiliser, relative to neburon, is 4%.

TABLE (I)

| Nature | Without stabiliser (prior art) | | | With stabiliser (according to the invention) | | |
|---|---|---|---|---|---|---|
|  | Date | | | | | |
|  | to | to +30 days at 50° C. | F/T | to | to +30 days at 50° C. | F/T |
| Self-dispersion | v.g. | 0 | m | v.g. | v.g. | v.g. |
| Dynamic viscosity in cp | 27.3 | non-pourable | 116 | 27.3 | 21.8 | 19.1 |
| Mean diameter in microns | 2.9 | 13.5 | 6.1 | 2.3 | 3.15 | 2.75 |

TABLE (II)

| Nature | Without stabiliser (prior art) | | | With stabiliser (according to the invention) | | |
|---|---|---|---|---|---|---|
|  | Date | | | | | |
|  | to | to +30 days at 50° C. | F/T | to | to +30 days at 50° C. | F/T |
| Self-dispersion | v.g. | 0 | m | v.g. | v.g. | v.g. |
| Dynamic viscosity in cp | 34 | 218 | 50.4 | 34 | 49.1 | 23.2 |
| Mean diameter in microns | 2.7 | 4.1 | 3.15 | 2.5 | 2.83 | 2.85 |

What is claimed is:

1. A herbicidal composition based on neburon, in the form of a concentrated aqueous suspension containing neburon and, optionally, thickening, wetting and/or dispersing adjuvants, which composition alo contains a nonphytotoxic amount of from 1 to 10% by weight, relative to neburon, of a stabiliser of the formula:

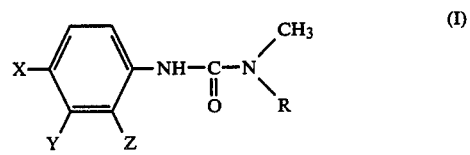

in which:
   X, Y and Z are identical or different and each represents a hydrogen atom, a halogen atom or an optionally halogenated alkyl radical containing from 1 to 4 carbon atoms and R represents an alkyl radical containing from 1 to 3 carbon atoms.

2. A herbicidal composition according to claim 1, in which the stabiliser is a compound of the formula:

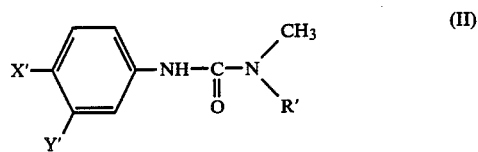

in which:
   R' represents a methyl or ethyl radical, X' represents a hydrogen atom, a halogen atom or an alkyl radical containing from 1 to 4 carbon atoms and Y' represents a hydrogen or haloen atom or a trifluoromethyl radical.

3. A herbicidal composition according to claim 2, in which, in the formula (II), X' is a chlorine or bromine atom or a methyl radical and Y' is either hydrogen, if X' is a chlorine or bromine atom, or a chlorine or bromine atom.

4. A herbicidal composition according to one of claims 1 to 3, in which, in the formula, the halogen atoms are chlorine atoms.

5. A herbicidal composition according to claim 4, in which the stabiliser is 3-(3,4-dichlorophenyl)-1,1-dimethylurea.

6. A herbicidal composition according to claim 4, in which the stabiliser is 3-(4-chlorophenyl)-1,1-dimethylurea.

7. A herbicidal composition according to claim 4, in which the stabiliser is 3-(3-chloro-4-methylphenyl)-1,1-dimethylurea.

8. A herbicidal composition according to claim 1, which contains from 2 to 6% by weight of stabiliser, relative to neburon.

9. A herbicidal composition according to claim 1, in which at least 95% by weight of the solid particles in suspension have a diameter of less than 20 microns, 50% by weight having a diameter of less than 7 microns.

10. A composition according to claim 1, which contains, as the active ingredient, neburon together with an herbicidally effective amount of at least one other herbicide which does not substantially modify the stability of the neburon in said composition.

11. A composition according to claim 10, in which the other herbicide is isoproturon.

12. A composition according to claim 10, in which the other herbicide is nitrofen.

13. A composition according to claim 10, in which the other herbicide is bifenox.

14. A composition according to claim 10, in which the other herbicide is terbutryn or atrazine.

* * * * *